United States Patent
Follenius

(10) Patent No.: US 9,750,633 B1
(45) Date of Patent: Sep. 5, 2017

(54) WATERPROOF COVER FOR AN OSTOMY POUCH

(71) Applicant: Arthur J Follenius, Jacksonville, FL (US)

(72) Inventor: Arthur J Follenius, Jacksonville, FL (US)

( * ) Notice: Subject to any disclaimer, the term of this patent is extended or adjusted under 35 U.S.C. 154(b) by 0 days.

(21) Appl. No.: 15/246,775

(22) Filed: Aug. 25, 2016

(51) Int. Cl.
*A61F 5/445* (2006.01)
*A61F 5/443* (2006.01)

(52) U.S. Cl.
CPC .............. *A61F 5/445* (2013.01); *A61F 5/443* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,387,713 A * | 6/1983 | Calanni | A61F 5/445 | 600/573 |
| 4,826,495 A * | 5/1989 | Petersen | A61F 5/441 | 604/333 |
| 5,248,308 A * | 9/1993 | von Emster | A61F 5/445 | 604/332 |
| 5,591,144 A * | 1/1997 | Smith | A61F 5/445 | 604/327 |
| 5,607,412 A * | 3/1997 | Brown | A61F 5/445 | 2/46 |
| 5,722,965 A * | 3/1998 | Kuczynski | A61F 5/448 | 604/338 |
| 5,769,831 A * | 6/1998 | Freeman | A61F 5/445 | 604/332 |
| 5,843,054 A * | 12/1998 | Honig | A61F 5/445 | 604/332 |
| 5,865,819 A * | 2/1999 | Cisko, Jr. | A61F 5/445 | 604/327 |
| 5,938,647 A * | 8/1999 | Smith | A61F 5/445 | 128/DIG. 24 |
| 6,186,989 B1 * | 2/2001 | Horie | A61F 5/445 | 604/345 |
| 7,722,586 B2 * | 5/2010 | Mullejans | A61F 5/441 | 604/332 |
| D624,644 S * | 9/2010 | Rago | A61F 5/445 | D24/118 |
| 8,377,020 B1 | 2/2013 | Berven | | |
| 8,439,883 B1 * | 5/2013 | Johnsen | A61F 5/448 | 604/338 |
| 2004/0059306 A1 * | 3/2004 | Tsal | A61F 5/4404 | 604/332 |
| 2005/0143696 A1 * | 6/2005 | Pedersen | A61F 5/448 | 604/332 |

(Continued)

*Primary Examiner* — Todd J Scherbel
*Assistant Examiner* — Guy K Townsend
(74) *Attorney, Agent, or Firm* — Kintner IP, LLC; Mary Frances Ludwig

(57) ABSTRACT

A cover for an ostomy pouch comprises a flexible waterproof material and an opening sealable in a waterproof manner through which the ostomy pouch may pass. An aperture in the front side is sized to closely surround an orifice of the ostomy pouch. A flange extends outward from the aperture and is sized to cover any portion of the ostomy pouch which projects through the aperture. An adhesive layer contacts the flange and adheres removably to the skin of the wearer. In an embodiment, a resilient ring surrounds the aperture. Reusable and disposable versions of the cover are provided.

12 Claims, 3 Drawing Sheets

(56) References Cited

U.S. PATENT DOCUMENTS

| | | | |
|---|---|---|---|
| 2005/0177119 A1* | 8/2005 | Tsai | A61F 5/445 604/332 |
| 2007/0219514 A1* | 9/2007 | Strobech | A61F 5/448 604/336 |
| 2007/0260206 A1* | 11/2007 | Mullejans | A61F 5/445 604/332 |
| 2007/0282284 A1* | 12/2007 | Mullejans | A61F 5/4404 604/333 |
| 2008/0294129 A1* | 11/2008 | Giori | A61F 5/445 604/332 |
| 2010/0324511 A1* | 12/2010 | Dove | A61F 5/445 604/342 |
| 2011/0054425 A1* | 3/2011 | Smith | A61F 5/448 604/342 |
| 2011/0238024 A1* | 9/2011 | Smith | A61F 5/445 604/336 |

\* cited by examiner

WATERPROOF COVER FOR AN OSTOMY POUCH

CROSS REFERENCE TO RELATED APPLICATION

None

TECHNICAL FIELD

The present invention pertains generally to ostomy appliances, and more particularly to a waterproof cover for an ostomy pouch.

BACKGROUND OF THE INVENTION

Ostomy appliances require protection during exposure to water, such as when showering. Common two piece ostomy appliances comprise a wafer attachable to the stoma and a bag removably attachable to the wafer. For reasons of comfort, convenience, and cost a patient may desire to reuse the wafer while changing the bag multiple times. It is therefore highly desirable to protect the wafer from water damage as well as the bag.

Therefore a need exists for a waterproof ostomy cover which protects the entirety of a two part ostomy appliance, as well as being usable for one piece ostomy pouches. It is further desirable that such a cover be useful for a broad range of ostomy patients, including urostomy, colostomy, ileostomy, and others. It is further desirable that the cover be provided in both a reusable embodiment for patient home use and a single use embodiment for environments requiring sterile conditions, such as hospitals.

BRIEF SUMMARY OF THE INVENTION

The present invention is directed to a waterproof cover for an ostomy pouch suitable for protecting a broad range of ostomy appliances, including those used by colostomy, urostomy, and ileostomy patients. The cover protects both the ostomy bag and the wafer of two-part ostomy appliances from casual water exposure, such as encountered while showering. Both reusable and disposable covers are described herein.

In accordance with an embodiment of the cover for an ostomy pouch, an ostomy appliance cover system comprises a cover configured for use with a one piece or two piece ostomy appliance comprising an ostomy pouch comprising an orifice with an attached connecting ring configured to be removably or permanently adhered to a complementary ring of a wafer adherable to a patient's skin around a stoma. The cover includes a front side and a rear side each comprised of a flexible waterproof material. The outer edges of the front and rear sides of the cover are joined together and configured to enclose an interior region of the cover that is shaped and dimensioned to contain the ostomy pouch. The front side includes an expandable aperture configured to fit snugly around the connecting ring of the pouch and the complementary ring of the wafer when the pouch is adhered to the wafer. An opening in the cover is configured to separate and connect an upper edge of a lower portion to a lower edge of an upper portion of the front side or rear side of the cover. The upper edge and the lower edge are each attached to a complementary connecting portion of a fastener or interlocking seal. The opening is configured for the ostomy pouch to pass through into the interior region of the cover. The fastener or interlocking seal is configured to seal the upper portion to the lower portion in a waterproof manner. The expandable aperture in the front side of the cover is sized and configured to closely surround the connecting ring of the pouch and the complementary ring of the wafer. The aperture is configured for expansion such that the ostomy pouch can be removed from the wafer or the skin of the patient and pass through the expandable aperture, the interior region, and the opening of the cover, optionally, while the removably adhered or detached wafer remains external to the cover. The cover system further includes a waterproof flange having a distal face, a proximal face, a flange opening, and an outer periphery. The flange extends outward from the flange opening and the expandable aperture of the cover, and is sized and configured to overlap and extend beyond the outer periphery of the wafer. The cover system further comprises an adhesive layer comprising a distal adhesive side, a proximal adhesive side, and an adhesive layer opening. The adhesive layer is configured to adhere to the distal face or proximal face of the flange and to removably adhere to the skin of the patient around the stoma. The adhesive layer is further configured to, alternatively:

(i) the proximal adhesive side is configured to: (A) adhere to at least a periphery of the distal face of the flange; (B) extend beyond the outer periphery of the flange; and (C) removably adhere to the patient's skin to seal the flange around the wafer; and (ii) (A) the distal adhesive side is configured to removably adhere to the proximal face of the flange; and (B) the proximal adhesive side is configured to: (1) removably adhere to the patient's skin peripheral to the outer periphery of the wafer; and (2) seal the flange around the wafer;

such that the wafer of the ostomy appliance is protected from exposure to water exterior to the cover.

In accordance with another embodiment, the opening is in the front side.

In accordance with another embodiment, a resilient ring surrounds the aperture.

In accordance with another embodiment, the flange is comprised of vinyl plastic.

In accordance with another embodiment, the flange has a thickness greater than 375 micrometers.

In accordance with another embodiment, an adhesive layer contacts both the flange and the portion of the ostomy pouch which projects through the aperture.

Other embodiments, in addition to the embodiments enumerated above, will become apparent from the following detailed description, taken in conjunction with the accompanying drawings, which illustrate, by way of example, the principles of the ostomy pouch cover and method of use.

Figure 1:
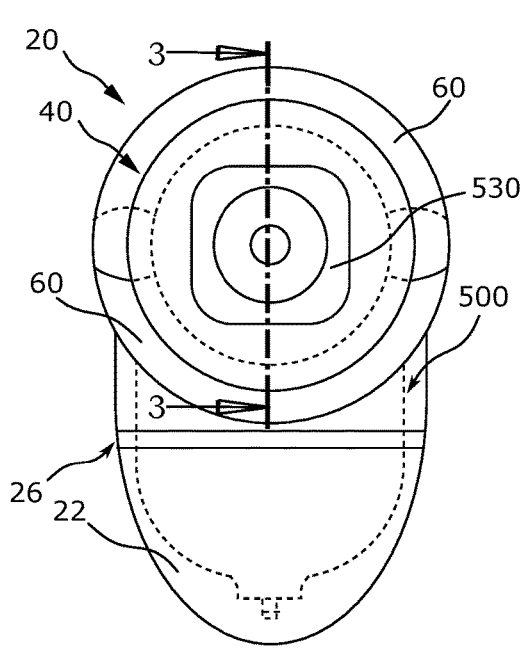
FIG. 1 is a front elevation view of a cover for an ostomy pouch.

LIST OF DRAWING REFERENCE NUMERALS 20 cover
22 front side
24 rear side
26 opening
30 aperture
32 resilient ring
40 flange
60 adhesive layer
500 ostomy pouch
510 orifice
520 ostomy bag
530 wafer
540 connecting ring
550 complementary ring

DETAILED DESCRIPTION OF THE INVENTION

Figure 2:
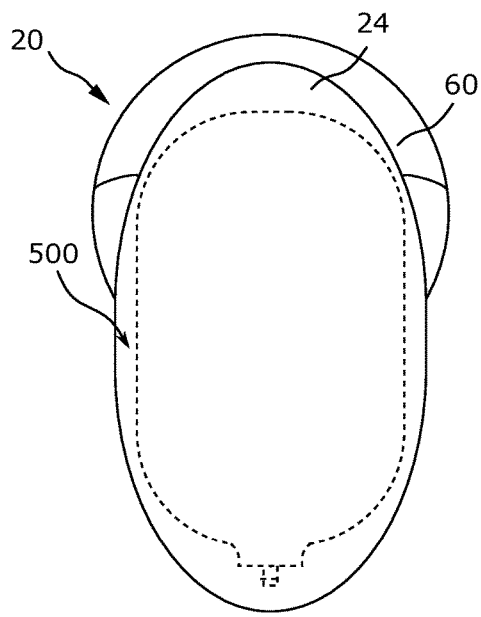
FIG. 2 is a rear elevation view of the cover.

Referring initially to FIGS. 1-2, there are illustrated front and rear elevation views respectively of a cover for an ostomy pouch, the cover generally designated as 20 and the ostomy pouch as 500. Cover 20 has a front side 22 and an opposite rear side 24. The terms 'front' or 'forward' indicate the direction facing the body of the wearer; the term 'rear' indicates the direction away from the wearer's body. Front side 22 and rear side 24 are joined together along their edges, enclosing an interior region which is shaped and dimensioned to contain ostomy pouch 500, as indicated with hidden lines in FIGS. 1 & 2.

Cover 20 is comprised of a flexible waterproof material, such as polyvinyl chloride or polyurethane laminated fabrics, low-density or high-density polyethylene, nitrile, and others well known in the art. As used herein, the term "waterproof" means keeping an item dry for at least 15 minutes while exposed to casual water contact, such as water spray in a shower.

Figure 3:
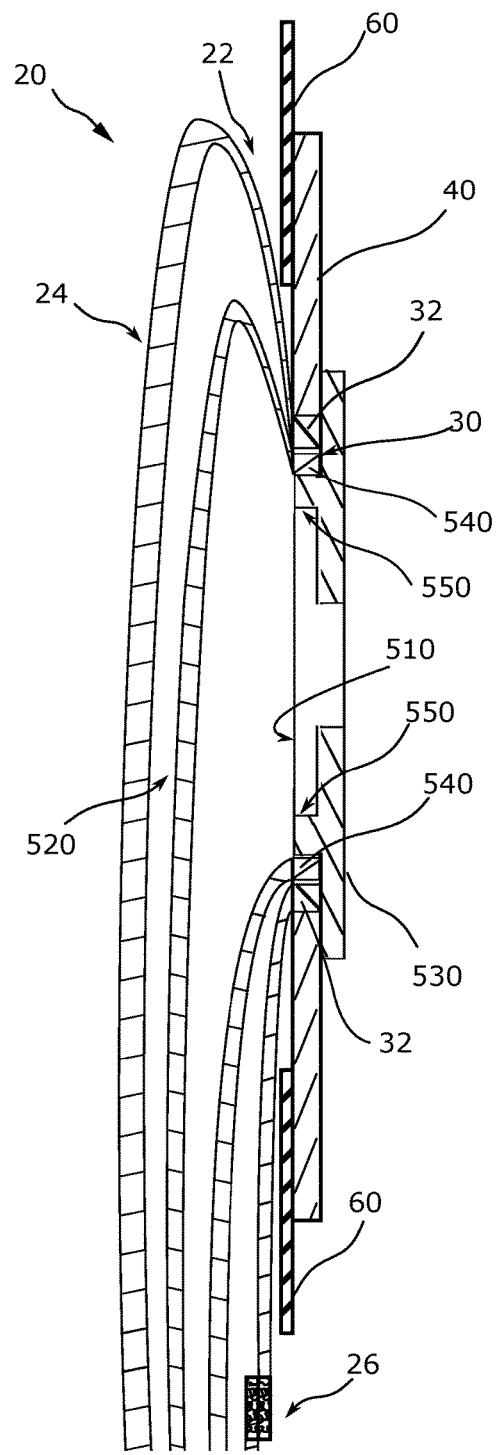
FIG. 3 is an enlarged cross-sectional view along the line 3-3 of FIG. 1.
Figure 4:
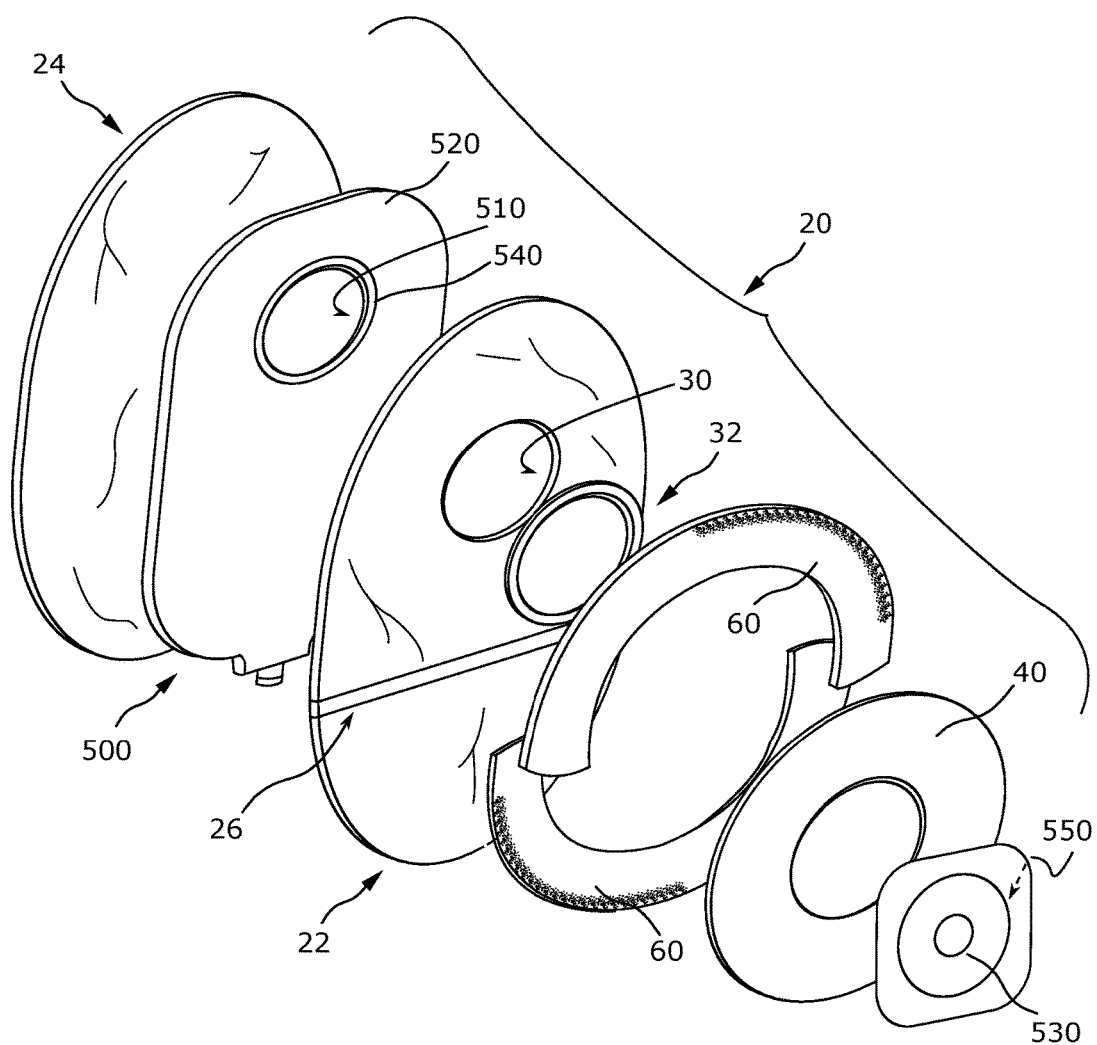
FIG. 4 is an exploded perspective view of the cover.

FIG. 3 is an enlarged cross-sectional view along the line 3-3 of FIG. 1, and FIG. 4 is an exploded perspective view of the cover. Ostomy pouch 500 has an orifice 510. In a two piece ostomy pouch, which includes an ostomy bag 520 and a wafer 530 (also commonly known as a baseplate, skin barrier, or flange), orifice 510 is the opening in ostomy bag 520 in the region where wafer 530 and bag 520 are connectable. A connecting ring 540 surrounds orifice 510 and is configured for removable attachment to a complementary ring 550 of wafer 530. In a single piece ostomy pouch, the orifice is in the region where the pouch attaches to the stoma. In a single piece ostomy pouch, connecting ring 540 is permanently adhered to complementary ring 550 of wafer 530. For example, in a single piece ostomy pouch, connecting ring 540 and complementary ring 550 are each bonding layers as is known in the art.

Cover 20 has an opening 26 through which the ostomy pouch is passed when inserted into cover 20. Opening 26 is sealable in a waterproof manner. In one embodiment of cover 20, opening 26 is sealable with a waterproof hook and loop fastener. In another embodiment, opening 26 comprises an interlocking groove and ridge that form a tight seal. In an embodiment, opening 26 is located on front side 22 to improve water resistance by proximity to the body of the wearer. In another embodiment, shown in FIG. 3, the exterior portion of opening 26 extends downward while the interior portion extends upward to further direct water away from entering cover 20.

In an embodiment where the cover is comprised of a waterproof fabric, front side 22 and rear side 24 are sewn together and heat treated after stitching for water tightness as is known in the art. In an embodiment where the cover is comprised of a plastic, front side 22 and rear side 24 are joined by heat-welding. In other embodiments, cover 20 is unitarily formed, and front and rear sides refer to the portions which are oriented forward and rearward when in use.

Figure 5:
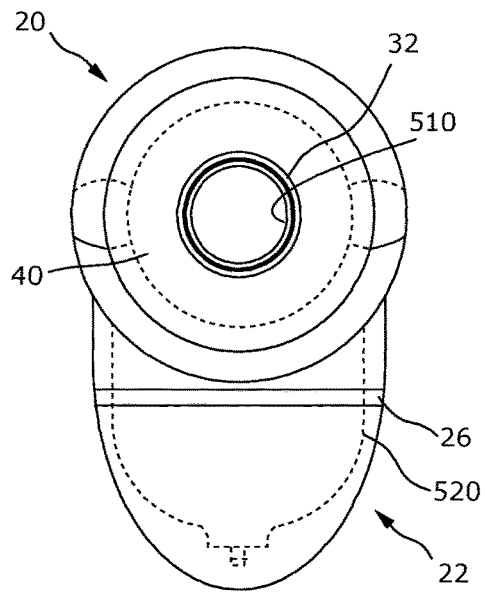
FIG. 5 is a front elevation view of the cover with one piece of a two piece ostomy pouch.
Figure 6:
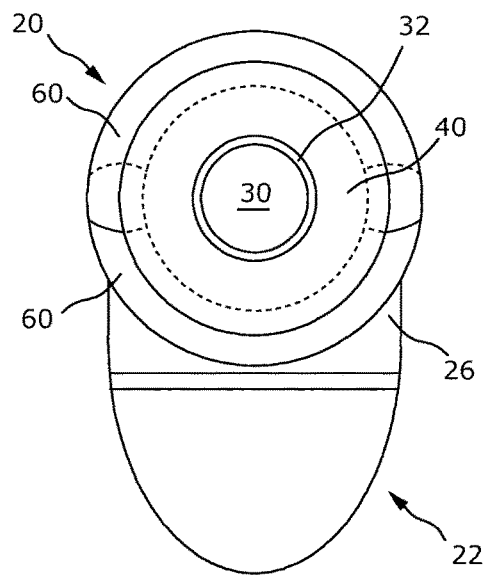
FIG. 6 is a front elevation view of the cover without the ostomy pouch.

FIG. 5 is a front elevation view of the cover with one piece of a two piece ostomy pouch and FIG. 6 is a front elevation view of the cover without the ostomy pouch. Cover 20 has an aperture 30 in front side 22 sized to closely surround orifice 510. A portion of ostomy pouch 500 adjoining orifice 510 may project through aperture 30 (see FIG. 3). For example, in the case of a two piece ostomy pouch, wafer 530 is located external to cover 20 and is connected to ostomy bag 520 at orifice 510 which is surrounded by aperture 30.

In an embodiment, a resilient ring 32 surrounds aperture 30. In one embodiment, ring 32 is comprised of a stretchable fabric. In another embodiment, ring 32 is comprised of the same material as front side 22. Ring 32 preferably provides an elastic fit without material gathering around aperture 30. The resiliency of ring 32 eases the process of putting the cover on, and enables a single aperture size to accommodate a range of ostomy wafer sizes. For example, an aperture size of about 65 mm will accommodate the wafer of a commercially available two-piece ostomy pouch sized for 10 mm to 25 mm stoma openings. An aperture size of about 75 mm will accommodate the wafer of a commercial pouch system sized for 15 mm to 35 mm stoma openings. These size ranges accommodate about 90% of the ostomy appliances in use.

A flange 40 extends outward from aperture 30 and is sized to cover any portion of ostomy pouch 500 which projects through aperture 30 (see FIGS. 1 & 3). Flange 40 comprises a waterproof material. In an embodiment, flange 40 is comprised of vinyl plastic. In a reusable embodiment of cover 20, flange 40 has a thickness of greater than 20 mils (about 500 micrometers). In a disposable embodiment, flange 40 has a thickness of between 15 mils and 20 mils (about 375 to about 500 micrometers).

As used in this application, the term "about" or "approximately" refers to a range of values within plus or minus 10% of the specified number.

An adhesive layer 60 contacts flange 40 and is removably adherable to the skin of the patient. In the embodiments of FIGS. 1-6, adhesive layer 60 comprises two semi-circular elastic barrier strips. These strips are sized to overlap one another (best shown in FIG. 4, overlapping hidden regions shown in dashed lines in FIGS. 1, 5, 6, & 8) so as to completely seal the perimeter of flange 40 to the wearer's skin. Adhesive 60 and flange 40 thereby provide a sealed waterproof barrier to any portion of ostomy pouch 500 not contained inside cover 20, such as wafer 530. The adhesive layer may be otherwise shaped and still perform the intended function.

Figure 7:
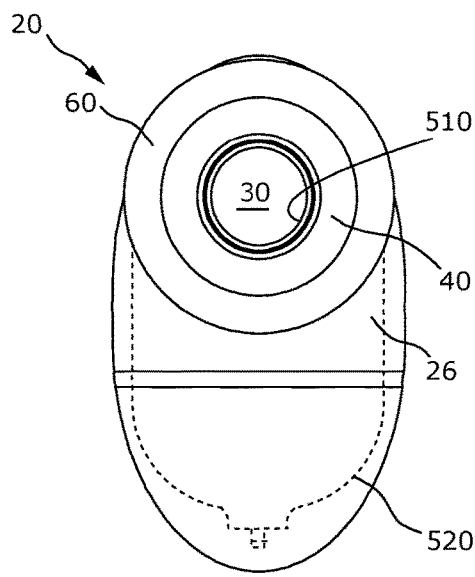
FIG. 7 is a front elevation view of another embodiment of the cover.

FIG. 7 is a front elevation view of another embodiment of cover 20. In this embodiment adhesive layer 60 comprises a double-sided adhesive, which contacts and adheres to both flange 40 and the wearer's skin. Adhesive layer 60 may comprise one or more adhesive strips. In the shown embodiment, adhesive layer 60 is a substantially circular ring, the rear face of which is entirely in contact with flange 40 and the front face of which is adherable to the wearer's skin. In another embodiment, adhesive layer 60 also contacts the portion of the ostomy pouch which projects through aperture 30.

Figure 8:
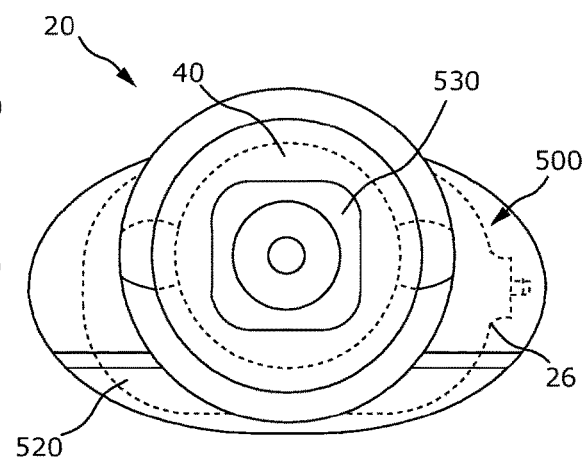
FIG. 8 is a front elevation view of another embodiment of the cover.

FIG. 8 is a front elevation view of another embodiment of cover 20, in which the long axis of the cover is oriented horizontally instead of vertically. The shown orientation is more suitable for colostomy bags. The embodiment shown covers a two-piece colostomy bag 500. This embodiment comprises the same features and performs the same functions as the embodiment of FIGS. 1-6, the shape of which is more suitable for covering a urostomy bag.

In another embodiment, cover 20 cooperates with ostomy pouch 500 to form a waterproof ostomy pouch system.

Further provided are reusable and disposable versions of the embodiments described herein. Materials, waterproofing treatments, and sealable openings are disclosed which are suitable for both reusable and disposable covers.

In terms of use, a method for a patient having skin to protect an ostomy pouch 500 from water, ostomy pouch 500 having an orifice 510, the method including: (refer to FIGS. 1-8)
- (a) providing a cover 20 comprised of a flexible waterproof material, the cover including:
  - (i) a front side 22 facing the skin;
  - (ii) an opening 26 sealable in a waterproof manner;
  - (iii) an aperture 30 in front side 22 sized to closely surround orifice 510;
  - (iv) a flange 40 extending outward from aperture 30; and,
  - (v) an adhesive layer 60 contacting flange 40;
- (b) passing ostomy pouch 500 through opening 26;
- (c) sealing opening 26;
- (d) positioning ostomy pouch 500 so that orifice 510 is closely surrounded by aperture 30; and,
- (e) adhering adhesive layer 60 to the skin.

The method further including:
in (a), a resilient ring 32 surrounding aperture 30; and, after (b), a portion of ostomy pouch 500 adjoining orifice 510 projecting through the aperture.

The embodiments of the cover for an ostomy pouch and method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the cover and method should be construed as limiting the invention to a particular embodiment or combination of embodiments. The scope of the invention is defined by the appended claims.

I claim:

1. An ostomy appliance cover system comprising a cover configured for use with a one piece or two piece ostomy appliance comprising an ostomy pouch comprising an orifice with an attached connecting ring configured to be removably or permanently adhered to a complementary ring of a wafer adherable to a patient's skin around a stoma, the wafer having an outer periphery, the ostomy appliance cover system comprising:
   (a) the cover, the cover comprising:
      (i) a front side comprising an expandable aperture configured to fit snugly around the connecting ring of the pouch and the complementary ring of the wafer when adhered;
      (ii) a rear side, wherein the front side and rear side are each comprised of a flexible waterproof material having front and rear outer edges joined together and configured to enclose an interior region of the cover that is shaped and dimensioned to contain the ostomy pouch;
      (iii) an opening configured to separate and connect an upper edge of a lower portion to a lower edge of an upper portion of the front side or rear side of the cover, the upper edge and the lower edge each attached to a complementary connecting portion of a fastener or interlocking seal, the opening configured for the ostomy pouch to pass through into the interior region of the cover, the fastener or interlocking seal configured to seal the upper portion to the lower portion in a waterproof manner;
   wherein the expandable aperture in the front side of the cover is: sized and configured to closely surround the connecting ring of the pouch and the complementary ring of the wafer; and configured for expansion such that the ostomy pouch can be inserted through the expandable aperture into the interior region of the cover while the adhered or detached wafer remains external to the cover;
   (b) a waterproof flange having a distal face, a proximal face, a flange opening, and an outer periphery, the flange extending outward from the flange opening and the expandable aperture of the cover, and sized and configured to overlap and extend beyond the outer periphery of the wafer; and,
   (c) an adhesive layer comprising a distal adhesive side, a proximal adhesive side, and an adhesive layer opening, the adhesive layer configured to adhere to the distal face or proximal face of the flange and to removably adhere to the skin of the patient around the stoma, wherein the adhesive layer is configured to, alternatively:
      (i) the proximal adhesive side is configured to: (A) adhere to at least a periphery of the distal face of the flange; (B) extend beyond the outer periphery of the flange; and (C) removably adhere to the patient's skin to seal the flange around the wafer; and,
      (ii) (A) the distal adhesive side is configured to removably adhere to the proximal face of the flange; and (B) the proximal adhesive side is configured to: (1) removably adhere to the patient's skin peripheral to the outer periphery of the wafer; and (2) seal the flange around the wafer;
   such that the wafer of the ostomy appliance is protected from exposure to water exterior to the cover.

2. The cover according to claim 1, wherein:
the opening is in the front side of the cover and the upper edge and the lower edge are provided below the aperture.

3. The cover according to claim 1, further including:
a resilient ring surrounding the aperture.

4. The cover according to claim 1, wherein:
the flange is comprised of vinyl plastic.

5. The cover according to claim 1, wherein:
the flange has a thickness greater than 375 micrometers.

6. A waterproof ostomy pouch system for a patient having skin, the system comprising:
   (a) a one piece or two piece ostomy appliance comprising an ostomy pouch comprising an orifice with an attached connecting ring configured to be removably or permanently adhered to a complementary ring of a wafer adherable to the patient's skin around a stoma, the wafer having an outer periphery;

(b) a cover, the cover comprising:
  (i) a front side comprising an expandable aperture configured to fit snugly around the connecting ring of the pouch and the complementary ring of the wafer when adhered;
  (ii) a rear side, wherein the front side and rear side are each comprised of a flexible waterproof material having front and rear outer edges joined together and configured to enclose an interior region of the cover that is shaped and dimensioned to contain the ostomy pouch;
  (iii) an opening configured to separate and connect an upper edge of a lower portion to a lower edge of an upper portion of the front side or rear side of the cover, the upper edge and the lower edge each attached to a complementary connecting portion of a fastener or interlocking seal, the opening configured for the ostomy pouch to pass through into the interior region of the cover, the fastener or interlocking seal configured to seal the upper portion to the lower portion in a waterproof manner;
  wherein the expandable aperture in the front side of the cover is: sized and configured to closely surround the connecting ring of the pouch and the complementary ring of the wafer; and configured for expansion such that the ostomy pouch can be inserted through the expandable aperture into the interior region of the cover while the adhered or detached wafer remains external to the cover;
(c) a waterproof flange having a distal face, a proximal face, a flange opening, and an outer periphery, the flange extending outward from the flange opening and the expandable aperture of the cover, and sized and configured to overlap and extend beyond the outer periphery of the wafer; and,
(d) an adhesive layer comprising a distal adhesive side, a proximal adhesive side, and an adhesive layer opening, the adhesive layer configured to adhere to the distal face or proximal face of the flange and to removably adhere to the skin of the patient around the stoma, wherein the adhesive layer is configured to, alternatively:
  (i) the proximal adhesive side is configured to: (A) adhere to at least a periphery of the distal face of the flange; (B) extend beyond the outer periphery of the flange; and (C) removably adhere to the patient's skin to seal the flange around the wafer; and,
  (ii) (A) the distal adhesive side is configured to removably adhere to the proximal face of the flange; and (B) the proximal adhesive side is configured to: (1) removably adhere to the patient's skin peripheral to the outer periphery of the wafer; and (2) seal the flange around the wafer;
  such that the wafer of the ostomy appliance is protected from exposure to water exterior to the cover.

7. The system according to claim 6, wherein:
the opening is in the front side of the cover and the upper edge and the lower edge are provided below the aperture.

8. The system according to claim 6, further including:
a resilient ring surrounding the aperture.

9. The system according to claim 6, wherein:
the flange is comprised of vinyl plastic.

10. The system according to claim 6, wherein:
the flange has a thickness greater than 375 micrometers.

11. A method for a patient having skin to protect a one piece or two piece ostomy appliance from water, the ostomy appliance comprising an ostomy pouch comprising an orifice with an attached connecting ring configured to be removably or permanently adhered to a complementary ring of a wafer adherable to a patient's skin around a stoma, the wafer having an outer periphery, the method comprising:
  (a) providing an ostomy appliance cover system comprising:
    (i) a cover, the cover comprising:
      (A) a front side comprising an expandable aperture configured to fit snugly around the connecting ring of the pouch and the complementary ring of the wafer when adhered;
      (B) a rear side, wherein the front side and rear side are each comprised of a flexible waterproof material having front and rear outer edges joined together and configured to enclose an interior region of the cover that is shaped and dimensioned to contain the ostomy pouch; and,
      (C) an opening configured to separate and connect an upper edge of a lower portion to a lower edge of an upper portion of the front side or rear side of the cover, the upper edge and the lower edge each attached to a complementary connecting portion of a fastener or interlocking seal, the opening configured for the ostomy pouch to pass through into the interior region of the cover, the fastener or interlocking seal configured to seal the upper portion to the lower portion in a waterproof manner;
    wherein the expandable aperture in the front side of the cover is: sized and configured to closely surround the connecting ring of the pouch and the complementary ring of the wafer; and configured for expansion such that the ostomy pouch can be inserted through the expandable aperture into the interior region of the cover while the adhered or detached wafer remains external to the cover;
    (ii) a waterproof flange having a distal face, a proximal face, a flange opening, and an outer periphery, the flange extending outward from the flange opening and the expandable aperture of the cover and sized and configured to overlap and extend beyond the outer periphery of the wafer; and,
    (iii) an adhesive layer comprising a distal adhesive side, a proximal adhesive side, and an adhesive layer opening, the adhesive layer configured to adhere to the distal face or proximal face of the flange and to removably adhere to the skin of the patient around the stoma, wherein the adhesive layer is configured to, alternatively:
      (A) the proximal adhesive side is configured to: (1) adhere to at least a periphery of the distal face of the flange; (2) extend beyond the outer periphery of the flange; and (3) removably adhere to the patient's skin to seal the flange around the wafer; and,
      (B) (1) the distal adhesive side is configured to removably adhere to the proximal face of the flange; and (2) the proximal adhesive side is configured to: (a) removably adhere to the patient's skin peripheral to the outer periphery of the wafer; and (b) seal the flange around the wafer;
  (b) passing the ostomy pouch through the opening or the expandable aperture of the cover;
  (c) after b, sealing the fastener or interlocking seal of the opening of the cover;

(d) after b, positioning the ostomy pouch so that the connecting ring of the pouch is closely surrounded by the expandable aperture and the wafer remains external to the cover; and, (e) adhering the adhesive layer to the flange and the skin peripheral to the outer periphery of the wafer, the flange and adhesive layer thereby protecting the wafer of the ostomy appliance from exposure to water exterior to the cover.

12. The method according to claim 11, further including: in (a)(i)(A), a resilient ring surrounding the expandable aperture.

\* \* \* \* \*